United States Patent [19]
Roberts

[11] Patent Number: 5,686,281
[45] Date of Patent: Nov. 11, 1997

[54] CHIMERIC RECEPTOR MOLECULES FOR DELIVERY OF CO-STIMULATORY SIGNALS

[75] Inventor: Margo R. Roberts, San Francisco, Calif.

[73] Assignee: Cell Genesys, Inc., Foster City, Calif.

[21] Appl. No.: 455,860

[22] Filed: May 31, 1995

Related U.S. Application Data

[63] Continuation of Ser. No. 383,749, Feb. 3, 1995.
[51] Int. Cl.$^6$ .................................................. C12N 15/62
[52] U.S. Cl. .................... 435/172.3; 435/7.1; 435/7.2; 435/69.7; 536/23.4
[58] Field of Search ...................... 435/7.1, 7.2, 64.7, 435/172.3, 252.3, 320.1; 536/23.4

[56] References Cited

U.S. PATENT DOCUMENTS 5,359,046  10/1994  Capon et al. ........................... 435/69.7

OTHER PUBLICATIONS

Romeo et al., "Activation of . . . Intracellular Domains", Cold Spring Harbor Symposia on Quantitative Biology, vol. 57, 117 (1992).
Romeo et al, *Cell* 64:1037–1046, Mar. 8, 1991.
Romeo et al, *Cell* 68:889–897, Mar. 6, 1992.
Letourneur et al, *P.N.A.S.* 88:8905–8909, Oct. 1991.
Eshhar et al., *P.N.A.S.* 90:720–724, Jan. 1993.
Linsley et al., "The Role of the CD28 Receptor During T Cell Responses to Antigen," *Annu. Rev. Immunol.* 11:191–212 (1993).
June et al., "The B7 and CD28 receptor families," *Immunology Today* 15(7):321–331 (1994).
Schwartz, R.H., "Costimulation of T Lymphocytes: The Role of CD28, CTLA-4, and B7/BB1 in Interleukin-2 Production and Immunotherapy," *Cell* 71:1055–1068 (1992).
Stein et al., "The Cytoplasmic Domain of CD28 Is both Necessary and Sufficient for Costimulation of Interleukin–z Secretion and Association with Phosphatidylinositol 3'–Kinase," *Mol. and Cell. Biol.* 14(5):3392–3402 (1994).
Harding et al., "CD28–B7 Interactions Allow the Induction of CD8+ Cytotoxic T Lymphocytes in the Absence of Exogenous Help," *J. Exp. Med.* 177:1791–1796 (1993).
Riddell et al., "The use of anti–CD3 and anti–CD28 monoclonal antibodies to clone and expand human antigen–specific T cells," *J. of Immun. Methods* 128:189–201 (1990).

Chen et al., "Tumor Immunogenicity Determines the Effect of B7 Costimulation on T Cell–mediated Tumor Immunity," *J. Exp. Med.* 179:523–532 (1994).
Chen et al., "Costimulation of Antitumor Immunity by the B7 Counterreceptor for the T Lymphocyte Molecules CD28 and CTLA–4," *Cell* 71:1093–1102 (1992).
Baskar et al., "Constitutive expression of B7 restores immunogenicity of tumor cells expressing truncated major histocompatibility complex class II molecules," *PNAS* 90:5687–5690 (1993).
Beyers et al., "A Role in Transmembrane Signaling for the Cytoplasmic Domain of the CD2 T Lymphocyte Surface Antigen," *Cell* 54:979–984 (1988).
Bierer et al., "Synergistic T Cell Activation via the Physiological Ligands for CD2 and the T Cell Receptor," *J. Exp. Med.* 168:1145–1156 (1988).
Roberts et al., "Targeting of Human Immunodeficiency Virus–Infected Cells by CD8+ T Lymphocytes Armed with Universal T–Cell Receptors," *Blood* 84(9):2878–2889 (1994).
Irving & Weiss, "The Cytoplasmic Domain of . . . Transduction Pathways", Cell 64, 891–901, 1991.
Mastrangelo et al., "Gene Therapy . . . Clinicians", Sem. Oncol., 23(1)4–21 (1996).
Jain et al., "Barriers to . . . Tumors", Sci. Amer., 271(1)58–63 (1994).
Hynes & Groner, "A Target . . . Therapy", Nature Medicine, 1(7)631–2 (1995).
Glick & Pasternak, "Molecular Biotechnology" ASM Press (1993) pp. 113–114.

*Primary Examiner*—John Ulm
*Attorney, Agent, or Firm*—Sughrue,Mion,Zinn,Macpeak & Seas, PLLC

[57] ABSTRACT

The present invention is directed to novel chimeric co-stimulatory receptor proteins and DNA sequences encoding these proteins. The chimeric receptors comprise at least three domains in a single chain molecule: an extracellular ligand binding domain, a transmembrane domain and a cytoplasmic co-stimulatory effector function signaling domain that acts synergistically with an effector function signal in the host cell. Novel hybrid co-stimulatory receptor proteins include a second cytoplasmic effector function signaling domain. The invention further relates to expression cassettes containing the nucleic acids encoding the novel chimeric receptors, to host cells expressing the novel chimeric receptors and to methods of using the receptors to co-stimulate effector functions in the cells and for using cells expressing the receptors for treatment of cancer, disease and viral infections.

11 Claims, 3 Drawing Sheets

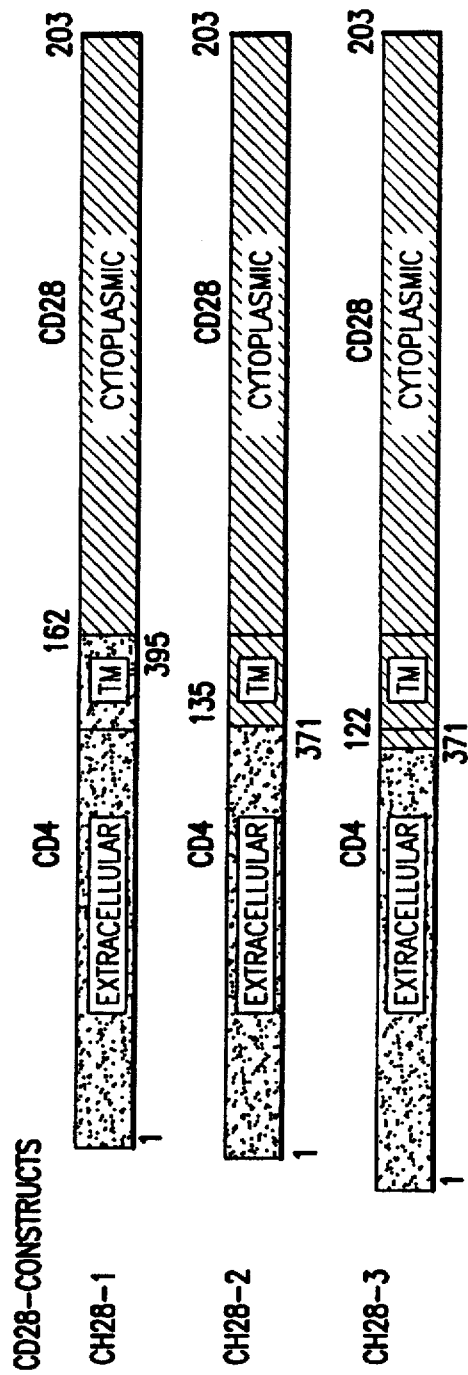
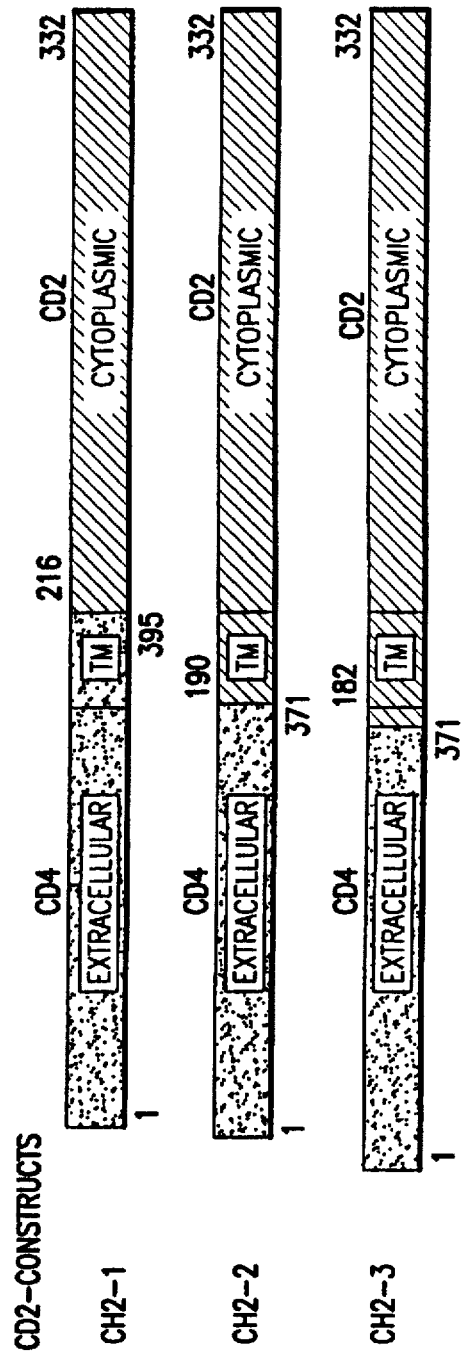
FIG.1A
FIG.1B

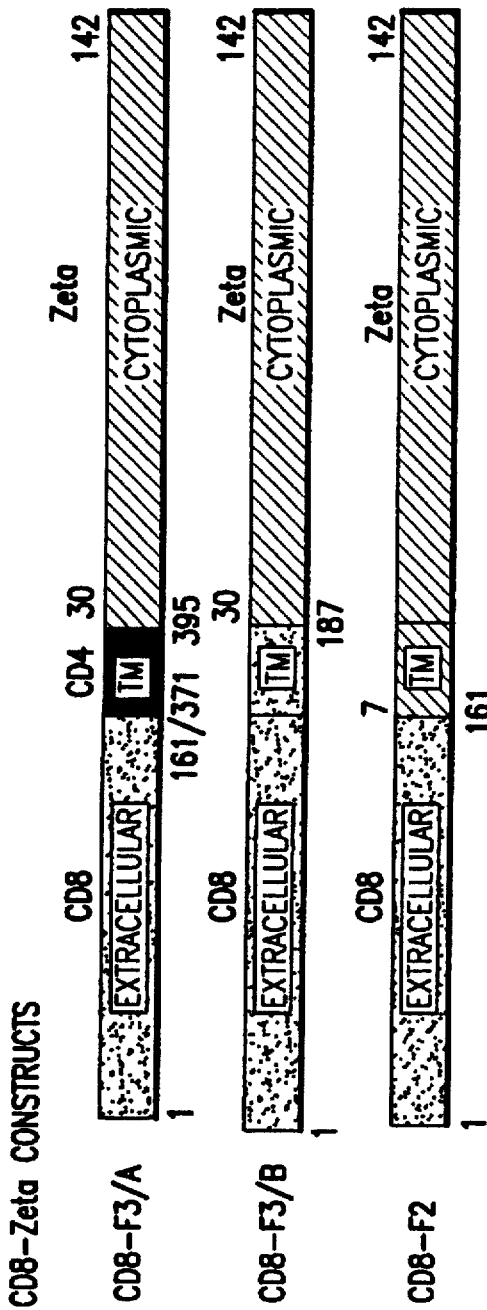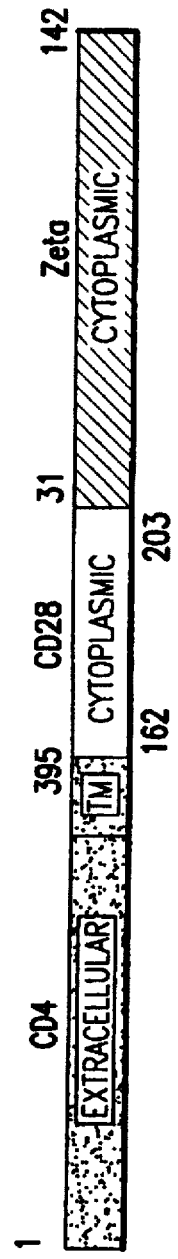

1.  CGTATTGGATCCGAGGAAACCAACCCCTAAG (SEQ ID NO:1)

2.  AATATTGGGCCCGGCAGAAATCCACAGTGC (SEQ ID NO:2)

3.  AATATTGGCGCCCCTAGCCCATCGTCAGGA (SEQ ID NO:3)

4.  AATATTGGATCCGGCTTCTGGATAGGCGTC (SEQ ID NO:4)

5.  CACCACCAGCACCCAAAATGGCTGCACCGGGGTGGA (SEQ ID NO:5)

6.  TAGGGGACTTGGACAAAGTGGCTGCACCGGGGTGGA (SEQ ID NO:6)

7.  CCTCTGTTTTTTCCTTTTGACACAGAAGAAGATGCC (SEQ ID NO:7)

8.  GCCAATGATGAGATAGATTGGCTGCACCGGGGTGGA (SEQ ID NO:8)

9.  ACCTTTCTCTGGACAGCTTGGCTGCACCGGGGTGGA (SEQ ID NO:9)

10. CCTGCTCCTCTTACTCCTCCGGCACCTGACACAGAA (SEQ ID NO:10)

11. CCTGCTCCTCTTACTCCTGAAGAAGATGCCTAGCCC (SEQ ID NO:11)

12. AATATTGAATTCCGAGCTTCGAGCCAA (SEQ ID NO:12)

13. AATATTGGTTACCAGTGGCTGTTGCACAGGG (SEQ ID NO:13)

14. CGCCCCCCAGCACAATCAGGGCCATTGCGCCCCCCG-
    CCGCCGCTGGCCGGCAC (SEQ ID NO:14)

15. CTGCGCTCCTGCTGAACTTCACTCTATTTGCAAACA-
    CGTCTTCGGTTCCT (SEQ ID NO:15)

16. CATCCAGCAGGTAGCAGAGTTTGGGTGCGCCCCCCG-
    CCGCTGGCCGGCAC (SEQ ID NO:16)

FIG. 2

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGTATTGGAT CCGAGGAAAC CAACCCCTAA G            31

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AATATTGGGC CCGGCAGAAA TCCACAGTGC            30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AATATTGGCG CCCCTAGCCC ATCGTCAGGA            30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single

```
            ( D ) TOPOLOGY: linear ( i i ) MOLECULE TYPE: DNA (genomic)

( x i ) SEQUENCE DESCRIPTION: SEQ ID NO:4:

AATATTGGAT  CCGGCTTCTG  GATAGGCGTC                                           30
```

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CACCACCAGC  ACCCAAAATG  GCTGCACCGG  GGTGGA                                   36
```

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
TAGGGGACTT  GGACAAAGTG  GCTGCACCGG  GGTGGA                                   36
```

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
CCTCTGTTTT  TTCCTTTTGA  CACAGAAGAA  GATGCC                                   36
```

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
GCCAATGATG  AGATAGATTG  GCTGCACCGG  GGTGGA                                   36
```

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
ACCTTTCTCT GGACAGCTTG GCTGCACCGG GGTGGA                                36
```

( 2 ) INFORMATION FOR SEQ ID NO:10:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

```
CCTGCTCCTC TTACTCCTCC GGCACCTGAC ACAGAA                                36
```

( 2 ) INFORMATION FOR SEQ ID NO:11:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

```
CCTGCTCCTC TTACTCCTGA AGAAGATGCC TAGCCC                                36
```

( 2 ) INFORMATION FOR SEQ ID NO:12:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

```
AATATTGAAT TCCGAGCTTC GAGCCAA                                          27
```

( 2 ) INFORMATION FOR SEQ ID NO:13:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

```
AATATTGGTT ACCAGTGGCT GTTGCACAGG G                                     31
```

( 2 ) INFORMATION FOR SEQ ID NO:14:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

```
CGCCCCCCAG CACAATCAGG GCCATTGCGC CCCCCGCCGC CGCTGGCCGG CAC             53
```

( 2 ) INFORMATION FOR SEQ ID NO:15:

(i) SEQUENCE CHARACTERISTICS:
 (A) LENGTH: 50 base pairs
 (B) TYPE: nucleic acid
 (C) STRANDEDNESS: single
 (D) TOPOLOGY: linear (ii) MOLECULE TYPE: DNA (genomic)

(xi) SEQUENCE DESCRIPTION: SEQ ID NO:15:

CTGCGCTCCT GCTGAACTTC ACTCTATTTG CAAACACGTC TTCGGTTCCT     50

(2) INFORMATION FOR SEQ ID NO:16:

(i) SEQUENCE CHARACTERISTICS:
 (A) LENGTH: 50 base pairs
 (B) TYPE: nucleic acid
 (C) STRANDEDNESS: single
 (D) TOPOLOGY: linear (ii) MOLECULE TYPE: DNA (genomic)

(xi) SEQUENCE DESCRIPTION: SEQ ID NO:16:

CATCCAGCAG GTAGCAGAGT TTGGGTGCGC CCCCCGCCGC TGGCCGGCAC     50

CHIMERIC RECEPTOR MOLECULES FOR DELIVERY OF CO-STIMULATORY SIGNALS

This application is a continuation of application Ser. No. 08/383,749, filed Feb. 3, 1995, which is pending.

TECHNICAL FIELD

The field of this invention relates to novel chimeric surface membrane proteins for use in co-stimulatory signal transduction.

BACKGROUND

Regulation of cell activities is frequently achieved by the binding of a ligand to a surface membrane receptor comprising an extracellular and a cytoplasmic domain. The formation of the complex between the ligand and the extracellular portion of the receptor results in a conformational change in the cytoplasmic portion of the receptor which results in a signal transduced within the cell. In some instances, the change in the cytoplasmic portion results in binding to other proteins, where other proteins are activated and may carry out various functions. In some situations, the cytoplasmic portion is autophosphorylated or phosphorylated, resulting in a change in its activity. These events are frequently coupled with secondary messengers, such as calcium, cyclic adenosine monophosphate, inositol phosphate, diacylglycerol, and the like. The binding of the ligand to the surface membrane receptor results in a particular signal being transduced.

Engagement of the TCR alone is not sufficient to induce activation of resting naive or memory T cells. Full, productive T cell activation requires a second co-stimulatory signal from a competent antigen-presenting cell (APC). Co-stimulation is achieved naturally by the interaction of the co-stimulatory cell surface receptor on the T cell with the appropriate counter-receptor on the surface of the APC. An APC is normally a cell of host origin which displays a moiety which will cause the stimulation of an immune response. APCs include monocyte/macrophages, dendritic cells, B cells, and any number of virally-infected or tumor cells which express a protein on their surface recognized by T cells. To be immunogenic APCs must also express on their surface a co-stimulatory molecule. Such APCs are capable of stimulating T cell proliferation, inducing cytokine production, and acting as targets for cytolytic T cells upon direct interaction with the T cell. (Linsley and Ledbetter, *Ann. Rev. Immunol.* 4:191–212 (1993); Johnson and Jenkins, *Life Sciences* 55:1767–1780 (1994); June et al., *Immunol. Today* 15:321–331 (1994); and Mondino and Jenkins, *J. Leuk. Biol.* 55:805–815 (1994)).

There are a number of situations in which the immune system fails to respond properly because the APCs lack the counter-receptor molecules necessary for co-stimulation. The result is an immune system which is paralyzed in response to that particular moiety.

For T lymphocytes in particular, induction of effector functions requires two biochemically distinct signals delivered through engagement of unique cell surface membrane receptors, usually one delivered through the T cell's specific antigen receptor (TCR) and the other via a so-called co-stimulatory receptor. Engagement of the co-stimulatory molecule together with the TCR is necessary for optimal levels of IL-2 production, proliferation and clonal expansion, and generation of effector functions such as the production of immunoregulatory cytokines, induction of antibody responses from B cells, and induction of cytolytic activity. More importantly, engagement of the TCR is the absence of the co-stimulatory signal results in a state of non-responsiveness, called anergy. Anergic cells fail to become activated upon subsequent stimulation through the TCR, even in the presence of co-stimulation, and in some cases may be induced to die by a programmed self-destruct mechanism.

In certain situations, for example where APCs lack the counter-receptor molecules necessary for co-stimulation, it would be beneficial to have the co-stimulatory signal induced by virtue of employing a ligand other than the natural ligand for the co-stimulatory receptor. This might be, for example, the same ligand as that recognized by the TCR (i.e., the same moiety, such that if one signal is received, both signals will be received), or another cell surface molecule known to be present on the target cells (APCs).

The primary co-stimulatory receptor is the CD28 molecule on T cells which interacts with a so-called "counter-receptor" ligand called B7 on APCs. Co-stimulation is achieved naturally by the interaction of the CD28 surface membrane receptor on T cells with the B7 counter-receptor on APCs.

CD28 is a homodimer of 44 kD subunits, a member of the immunoglobulin (Ig) gene superfamily. CD28 is expressed on thymocytes and the majority of mature T cells in peripheral lymphoid tissues. It is expressed on virtually all CD4+ T cells and approximately 50% of CD8+ T cells. The subpopulation of CD8 T cells expressing CD28 contains the precursors for cytotoxic effector cells, while the reciprocal population has the potential to act as suppressor cells (Linsley et al., 1993 supra).

The biochemical mechanism of CD28 signal transduction has not been clearly elucidated but it is clear that (i) CD28 stimulation alone is not sufficient to activate cells, and (ii) the signal mediated by CD28 must be different from the CD3/TCR signal because the CD28 signal synergizes with the CD3/TCR signal. A detailed summary of CD28 signal transduction can be found in June et al., 1994, supra, and Linsley and Ledbetter, 1993, supra. A hallmark of CD28 signaling is that it is at least partially resistant to CsA, and therefore must have a component which is independent to the calcium-dependent phosphatase calcineurin. This is in direct contrast to CD3/TCR signaling which is completely inhibited by CsA. CD28 signaling involves the activation of phosphoinositide (PI) 3-kinase. CD28 ligation at the cell surface results in phosphorylation of Tyr 191 in the cytoplasmic domain of CD28. This phosphorylation event in turn drives the association of CD28 with PI 2-kinase via the -Y-M-N-T-P-R- amino acid sequence motif in the cytoplasmic domain of CD28 and the SH3 domain of PI 3-kinase. The phosphorylation of CD28 at Tyr 191 is thought to be an important regulator of CD28 signaling. Activation of PI 3-kinase activates an undefined cascade of second messengers which complete the CD28 signal.

CD28 co-stimulation results in maximum IL-2 production and enhances secretion of several other immunoregulatory cytokines, in particular those associated with TH1 cells. Enhanced secretion of cytokines occurs by two mechanisms: (i) the stabilization of cytokine mRNA (Mondino and Jenkins (1994), supra) and (ii) an increase in the rate of transcription via a CD28 response element in the promoters of the affected cytokines (Thompson et al., *Proc. Natl. Acad. Sci. USA* 86:1333–1337 (1989); Fraser and Weiss, *Mol. Cell. Biol.* 12:4357–4363 (1992); and Fraser et al., *Science* 251:313–316 (1991)). Cytokine production by both CD4 and CD8 T cells has been reported to be enhanced. Among the cytokines whose production is increased by CD28 co-stimulation are: IL-2, γ-IFN, TNF-α, lymphotoxin, and GM-CSF (Thompson et al., supra; June et al., supra; Chen et al., *J. Exp. Med.* 179:523–532 (1994); Kuiper et al., *Immunology* 83:38–44 (1994); and Mondino and Jenkins, supra). Of importance is the possibility that CD28 co-stimulation could render CD8 cells capable of sufficient autocrine IL-2 production to be independent of exogenous "help" (Harding and Allison, *J. Exp. Med.* 177:1791–1796 (1993)) from CD4+ T cells for example, and/or trigger alternative signal transduction pathways which promote IL-2 independent proliferation (Riddell and Greenberg, *J. Immunol. Methods* 128:189–201 (1990)).

CD28 co-stimulation also results in an increase in the rate of cell division, although this may be secondary to the increase in IL-2 production. Furthermore, direct increases in thymidine incorporation in vitro are only seen at suboptimal concentrations of anti-CD3 (Thompson et al., supra). This increase in the rate of cell division can be translated to an increased cloning efficiency of antigen-specific T cell lines in vitro (Riddell and Greenberg, supra).

In contrast, lack of CD28 co-stimulation at the time of antigen encounter (or CD3/TCR stimulation) results in anergy, a state of specific un-responsiveness. Antibodies to B7 or soluble ligands such as CTLA-Ig (Linsley et al. *J. Exp. Med.* 174:561–569 (1991)) have been used in Vitro and in vivo to block antigen-specific immune responses and prevent graft rejection (Thompson et al., supra; Fraser and Weiss, supra; and Fraser et al., supra) by interfering with the interaction between B7 and CD28 (Johnson and Jenkins, supra; Schwartz, R. H., *Cell* 71:1065–1068 (1992); Linsley and Ledbetter, supra). Antibodies to CD28 can substitute for co-stimulation by APCs in inducing immune responses and protecting T cells from anergy (Johnson and Jenkins, supra, and Linsley and Ledbetter, supra).

In certain tumor models, in vitro and in vivo, lack of expression of co-stimulatory molecules by tumor cells correlates with the ability to evade immunological destruction. This effect can be reversed by engineering the tumor cells to express B7 as shown by treatment of experimental tumors in animals and in vitro T cell responses to tumor cells transduced with B7 (Chen et al., *Cell* 71:1093–1102 (1992); Schwartz et al., supra; Jung et al., PNAS 84:4611–4615 (1987); Guo et al., *Science* 263:518–520 (1994); Chen et al., *Cancer Res.* 54:5420–5423 (1994); Hodge et al., *Cancer Res.* 54:5552–5555 (1994); Li et al., *J. Immunol.* 153:421–428 (1994); Townsend and Allison, *Science* 259:368- (1993); Booker et al., PNAS 90:5687–5690 (1993); Chen et al., *J. Exp. Med.* 179:523–532 (1994); and Harding and Allison (1993), supra).

Decreased CD28 expression in both CD4 and CD8 T cell populations from HIV-infected individuals correlates with defects in T cell function, tendency to undergo activation-induced apoptosis, and disease progression. Correction of defects in T cell function and protection from apoptosis (a programmed cell death mechanism initiated by aberrant signal transduction) is observed in vitro when cells are cultured with anti-CD28 antibodies (Brinchman et al., *J. Inf. Dis.* 169:730–738 (1994); Caruso et al., *Scand. J. Immunol.* 40:485–490 (1994); Landay et al., *Clin. Immunol. Immunopathol.* 69:106–116 (1993); Gougeon et al., *Science* 260:1269–1270 (1993); Groux et al., *J. Exp. Med,* 175:331–340 (1992); Meyaard et al., *Science* 257:217–219 (1992); and Choremi-Papadopoulou et al., *J. Aids* 7:245–253 (1994)).

A second receptor, CTLA-4, bears significant structural homology to CD28 and interacts with the same B7 family counter-receptors as CD28 (Linsley and Ledbetter, supra; June et al., supra, and Mondino and Jenkins, supra)). CTLA-4 was identified in a cDNA library made from murine cytolytic T lymphocytes (Linsley and Ledbetter, supra). CTLA-4 and CD28 share the same intron and exon organization and are genetically linked on human chromosome 2. Like CD28, CTLA-4 has a putative PI 3-kinase interaction motif in its cytoplasmic tail. CTLA-4 expression is induced in activated T cells (expression is restricted to the CD28+ populations), and is expressed in lower amounts on the cell surface than CD28, but has a much higher affinity for the B7 family counter-receptors. The level of homology between CTLA-4 and CD28 suggests that CTLA-4 signaling proceeds via a biochemical pathway similar to that of CD28 and that it performs a complementary signaling role to CD 28.

Another receptor molecule, CD2, found on virtually all thymocytes and T cells, has also been shown to synergize with CD3/TCR stimulation to augment T cell activation (Bierer et al., *J. Exp. M.* 168:1145 (1988)). CD2 is a 50 kd single chain surface membrane glycoprotein with two immunoglobulin-like extracellular domains (Williams, *Immunol. Today* 8:298–303 (1987)), a transmembrane domain, and a cytoplasmic domain which is involved in signal transduction (He et al., *Cell* 54:979–985 (1988)). In contrast to CD28 and CTLA-4, which alone are unable to activate T cells, the use of monoclonal antibodies (anti-T11$_1$ and anti-T11$_2$) which bind to distinct epitopes on CD 2, together, induce T cell proliferation and cytokine production (Meuer et al., *Cell* 36:897 (1984)). However, activation of T cells via CD2 is dependent on the expression in the cell of the zeta chain of CD3 (Howard et al., *J. Exp. Med.* 176:139–145 (1992)).

In addition to CD28, CTLA-4, CD2, several other surface receptors have been reported to provide co-stimulation for T cell activation through the CD3/TCR. These include, for example, CD5, ICAM-1, LFA-1 (CD11a/CD18) (Ledbetter et al., *J. Immunol.* 135:2331 (1985); Damle et al., *J. Immunol.* 148:1985–1992; Mondino and Jenkins, *J. Leuk. Biol.* 55:805–815 (1994)). The signaling pathways utilized by these co-stimulatory molecules share the common property of acting in synergy with the primary T cell receptor activation signal.

The production of chimeric effector function receptor proteins which initiate signaling in a cell that results in activation of a second messenger pathway in response to an inducer binding to the extracellular portion of these receptors is the subject of U.S. Pat. No. 5,359,046, the disclosure of which is incorporated in its entirety herein. These chimeric effector function receptor proteins comprise three domains in a single protein moiety, namely an extracellular ligand binding domain, a cytoplasmic effector function signaling domain and a transmembrane domain linking the extracellular and cytoplasmic domain together. The cytoplasmic domain and extracellular domain are not naturally associated. These chimeric effector function receptors can transduce a signal in their host cells in response to the binding of different ligands, in a non-MHC restricted fashion, to the extracellular domain. These receptors are useful for directing the activity of cells expressing the receptors for a particular effector functional.

A co-stimulatory chimeric receptor in which an extracellular ligand binding domain is linked to the signal transducing domain of a co-stimulatory molecule, such as CD28, could have as its target virtually any cell surface moiety of interest. Using such chimeric receptors, the ligand which provides co-stimulation may be selected to support a desired immune response where for some reason the natural ligand is missing or less useful. The co-stimulatory receptor could provide a signal that is synergistic with the primary effector activation signal, i.e. the TCR signal or the chimeric effector function receptor signal, and can complete the requirements for activation under conditions where stimulation of the TCR or chimeric effector function receptor is suboptimal and might otherwise be detrimental to the function of the cell. These receptors can support immune responses, particularly of T cells, by permitting the use of ligands other than the natural ligand to provide the required co-stimulatory signal.

SUMMARY OF THE INVENTION

Novel co-stimulatory receptor chimeric DNA sequences, expression cassettes and vectors containing these sequences, as well as cells containing the chimeric DNA and novel chimeric receptor proteins expressed from the sequences, are provided where the novel co-stimulatory chimeric DNA sequences comprise three domains which do not naturally exist together: (1) at least one cytoplasmic domain, which normally transduces a co-stimulatory signal resulting in activation of a messenger system, (2) at least one transmembrane domain, which crosses the outer cellular membrane, and (3) at least one extracellular receptor domain which serves to bind to a ligand and transmit a signal to the cytoplasmic domain, resulting in a co-stimulatory signal in the host cell in which the chimeric DNA is expressed. Particularly, cytoplasmic DNA sequences of co-stimulatory molecules such as the CD28, CTLA-4 or CD2 cell surface receptors are employed joined to other than their natural extracellular domain by a transmembrane domain. In this manner, host cells that express the chimeric co-stimulatory receptor protein can receive the necessary co-stimulatory signal by contact with the ligand as contrasted with the normal mode of activation of the cytoplasmic domain. Additional embodiments of the co-stimulatory receptors include hybrid chimeric receptors which contain both a cytoplasmic domain such as a CD3 chain of the TCR, for example zeta, as well as a cytoplasmic domain derived from a co-stimulatory molecule such as CD28, in a single chain to provide both a TCR activation signal and a co-stimulatory signal in the host cell.

The DNA encoding the co-stimulatory chimeric receptors associated with regulatory sequences that permit the transcription and translation of the receptor gene and its expression in a host cell is transduced into a host cell for production of the co-stimulatory chimeric receptor protein. The present invention further includes methods of using the co-stimulatory chimeric receptors for cell proliferation and as therapeutics for treating cancer and disease.

DESCRIPTION OF THE DRAWINGS

FIG. 1 illustrates the structures of the co-stimulatory chimeric receptors of the invention.

FIG. 2 is a listing of oligonucleotides (SEQ ID NOS: 1-16) as described in the Examples, infra.

DETAILED DESCRIPTION OF THE SPECIFIC EMBODIMENTS

The present invention discloses novel co-stimulatory chimeric receptor proteins and DNA sequences encoding these novel proteins.

These receptors may be introduced into host cells such as lymphocytes to augment proliferation of the cells in vitro and in vivo. The receptors may be introduced into host cells already expressing a chimeric effector function receptor such as that described in U.S. Pat. No. 5,359,046, or the two types of receptors may be introduced together and co-expressed in the same host cell. Further aspects of the invention are discussed in detail below.

The delivery of co-stimulatory signals required for induction of effector function in T cells can be initiated by the co-stimulatory chimeric receptors of the invention having the ability to bind to different ligands. These co-stimulatory chimeric receptors can overcome the lack of counter-receptor expression by certain virally-infected cells, tumor cells, or otherwise potentially immunogenic target cells, and may avoid the possibility of inactivation of T cells upon encounter with soluble antigen (e.g., cell-free virus particles) in the absence of APCs.

Definitions

The term "effector function" refers to the specialized function of a differentiated cell. Effector function of a T cell, for example, may be cytolytic activity or helper activity including the secretion of cytokines.

The term "chimeric effector function receptor" refers to a chimeric receptor that comprises an extracellular domain, a transmembrane domain and a cytoplasmic domain as described in U.S. Pat. No. 5,359,046. The extracellular domain binds a ligand and transmits a signal to the cytoplasmic domain which transduces an effector function signal to the cell in which the receptor is expressed.

The term "effector function signal" refers to the effector function signal provided by the native T cell receptor (TCR) in a cell or by a chimeric effector function receptor protein expressed in a host cell upon binding of a ligand.

The term "co-stimulatory signal" refers to the activation signal generated by contact between a ligand and a co-stimulatory receptor molecule on a cell which acts in synergy with the primary effector function signal.

The term "co-stimulatory chimeric receptor" refers to a chimeric receptor that comprises an extracellular ligand binding domain, a transmembrane domain and a cytoplasmic co-stimulatory signaling domain. The extracellular domain and the cytoplasmic domain are not naturally found together on a single receptor protein.

In its general embodiments the present invention describes novel co-stimulatory chimeric receptor proteins, nucleic acid sequences encoding the receptors, the vectors containing the nucleic acid sequences encoding the receptors, host cells expressing the receptors and methods of using the receptors to augment effector function of cells, to augment lymphocyte proliferation, to protect lymphocytes from anergy. In one embodiment of the invention, a novel co-stimulatory chimeric receptor is provided containing an extracellular ligand binding domain and a cytoplasmic co-stimulatory signaling domain that do not naturally exist together as a single receptor protein.

The co-stimulatory chimeric receptors are designed for expression in cells, particularly lymphocytes, to augment proliferation and/or effector function of the cells in response to binding of a ligand to the extracellular domain of the chimeric receptor. The host cells bearing the receptors of the invention will expand in number (proliferate) in response to the binding of a ligand to the extracellular ligand binding domain. The extracellular domains include, but are not limited to cell surface differentiation antigens, e.g. CD4, CD8, etc., a secreted targeting molecule, e.g. interleukin-14 (IL-14), etc., a cell surface/secreted targeting molecule, e.g. an antibody (Ab) or single-chain antibody (Sab), antibody fragments, etc., a cell adhesion molecule, e.g. ICAM, LFA-1, etc., or portions or derivatives thereof.

The co-stimulatory chimeric receptor of the invention can be introduced and expressed in host cells containing native T cell receptors or expressing chimeric effector function signaling receptors as described in U.S. Pat. No. 5,359,046 to augment effector function of the cells, for example to increase cytolytic activity, to increase cytokine production, to augment proliferation or to protect the cells from anergy. In addition, differentiation and/or maturation of the host cells, e.g. native T cells, may be augmented by the co-stimulatory chimeric receptors of the invention.

Alternatively, hybrid chimeric receptor molecules comprising an extracellular ligand binding domain, a transmembrane domain and a combined cytoplasmic domain comprising an effector function signaling domain, e.g. zeta, linked to a co-stimulatory signaling domain, e.g. CD28, are introduced into host cells (FIG. 1B). Upon introduction of these novel hybrid co-stimulatory/effector function chimeric receptors into cells, both a primary effector function signal and a co-stimulatory signal can be regulated by addition of a single ligand that binds to the extracellular domain of the hybrid receptor.

If the co-stimulatory chimeric receptor of the invention is expressed in host cells already expressing the chimeric effector function receptors of U.S. Pat. No. 5,359,046, for example the CD4/zeta chimeric receptor, then the effector function of the dual chimeric receptor expressing cells, e.g. cytotoxicity or cytokine production, can be activated and/or augmented upon addition of the same ligand. Alternatively, the ligand that binds to the extracellular binding domain of the chimeric effector function receptor may differ from the ligand that binds to the extracellular domain of the co-stimulatory chimeric receptor. In that case, an effector function signal will only result if both ligands bind to their respective extracellular domains. This can optimize specificity of response of the host cell because it will require two different target molecules to signal effector function. For example, where one target ligand is associated with a particular cancer cell and the other target ligand is associated with a particular cell type, then the host cell will be directed to function only when both cells types are present.

The cytoplasmic domain of the co-stimulatory chimeric receptor proteins may be derived from a protein which is known to activate various messenger systems. The protein from which the cytoplasmic domain is derived need not have ligand binding capability by itself, it being sufficient that such protein may associate with another protein providing such capability.

Cytoplasmic regions of interest include CD28 and CTLA-4, CD2, CD5, ICAM-1, Leukocyte Functional Antigen (LFA-1) (CD11a/CD18) and Heat Soluble Antigen (HSA), and such other cytoplasmic regions capable of transmitting a co-stimulatory signal as a result of interacting with other proteins that bind to a ligand. A number of cytoplasmic regions or functional fragments or mutants thereof may be employed, generally ranging from about 50 to 500 amino acids, where the entire naturally occurring cytoplasmic region may be employed or only an active portion thereof.

While usually the entire cytoplasmic region will be employed, in many cases, it will not be necessary to use the entire chain. To the extent that a truncated portion may find use, such truncated portions may be used in place of the intact chain.

Additionally, the chimeric receptors of the invention include hybrid receptors that contain a cytoplasmic domain of the co-stimulatory molecule and the entire or a portion of the cytoplasmic domain of the CD3 chains of the T cell receptor, for example the zeta, eta, delta, gamma or epsilon chains of the T cell receptor, or the beta and gamma chains of the FceR1 receptor, B29, or a tyrosine kinase such as a member of the Syk tyrosine kinase family which activates cytolysis, Syk or ZAP-70, where the cytoplasmic domain is capable of activating effector function in a host cell. As an example, the C-terminus of a CD4/CD28 receptor is joined to the N-terminal residue of the cytoplasmic domain of zeta (amino acid residue 203 of CD28 cytoplasmic domain joined to residue 31 of the zeta cytoplasmic domain) by oligonucleotide directed splicing, resulting in a chimeric molecule with the extracellular and transmembrane portions of CD4 and the cytoplasmic domains of CD3-zeta and CD28 linked head-to-tail (see FIG. 1). Thus, binding of the appropriate ligand, e.g. gp120 to the extracellular domain (CD4) results in the transduction of both a primary activation signal and a co-stimulatory signal simultaneously.

The transmembrane domain may be contributed by the domain of the protein contributing the cytoplasmic portion, the domain of the protein contributing the extracellular portion, or a domain associated with a totally different protein. In some cases, it will be convenient to have the transmembrane domain naturally associated with one or the other of the other domains, particularly the extracellular domain. In some cases it will be desirable to employ the transmembrane domain of the zeta, eta or FceR1γ chains or related proteins or of the co-stimulatory proteins, for example CD28 or CTLA-4, which contain a cysteine residue capable of disulphide bonding, so that the resulting chimeric protein will be able to form disulphide linked dimers with itself, or with unmodified versions of the chains or co-stimulatory proteins. In some instances, the transmembrane domain will be selected to avoid binding of such domain to the transmembrane domain of the same or different surface membrane proteins to minimize interactions with other members of the receptor complex. In other cases it will be desirable to employ the transmembrane domain of zeta, eta, FceR1 γ1 or the co-stimulatory protein, in order to retain physical association with other cell surface receptors or proteins.

The extracellular domain may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent or disulfide-bonded complex.

In particular, the extracellular domain may consist of monomeric or dimeric immunoglobulin (Ig) molecules, or portions or modifications thereof, which are prepared in the following manner. The full-length IgG heavy chain comprising the VH, CH1, hinge, and the CH2 and CH3 (Fc) Ig domains is fused to the co-stimulatory cytoplasmic signalling domain via the appropriate transmembrane domain. If the VH domain alone is sufficient to confer antigen-specificity (so-called "single-domain antibodies"), homodimer formation of the Ig-co-stimulatory chimera is expected to be functionally bivalent with regard to antigen binding sites. If both the VH domain and the VL domain are necessary to generate a fully active binding site, both the IgH-co-stimulatory molecule and the full-length IgL chain are introduced into cells to generate an active antigen-binding site. Dimer formation resulting from the intermolecular Fc/hinge disulfide bonds results in the assembly of Ig-co-stimulatory chimeric receptors with extracellular domains resembling those of IgG antibodies. Derivatives of these chimeric receptors include those in which only portions of the heavy chain are employed in the fusion. For example, the VH domain (and the CH1 domain) of the heavy chain can be retained in the extracellular domain of the Ig-co-stimulatory chimera, but VH-dimers are not formed. As above, the full-length IgL chain can be introduced into cells to generate an active antigen-binding site.

The extracellular domain may consist of an Ig heavy chain which in turn may be covalently associated with an Ig light chain by virtue of the presence of the CH1 region, or may become covalently associated with other Ig heavy/light chain complexes by virtue of the presence of hinge, CH2 and CH3 domains. The two heavy/light chain complexes may have different specificities, thus creating a chimeric receptor which binds two distinct antigens. Depending on the function of the antibody, the desired structure and the signal transduction, the entire chain may be used or a truncated chain may be used, where all or a part of the CH1, CH2 or CH3 domains may be removed or all or part of the hinge region may be removed.

Because association of both the heavy and light V domains are required to generate a functional antigen binding site of high affinity, in order to generate an Ig chimeric receptor with the potential to bind antigen, a total of two molecules will typically need to be introduced into the host cell. Therefore, an alternative and preferred strategy is to introduce a single molecule bearing a functional antigen binding site. This avoids the technical difficulties that may attend the introduction and coordinated expression of more than one gene construct into host cells. This "single-chain antibody" (SAb) is created by fusing together the variable domains of the heavy and light chains using an oligo- or polypeptide linker, thereby reconstituting an antigen binding site on a single molecule.

Single-chain antibody variable fragments (SAbFv) in which the C-terminus of one variable domain (VH or VL) is tethered to the N-terminus of the other (VL or VH, respectively), via a oligo- or polypeptide linker, have been developed without significantly disrupting antigen binding or specificity of the binding (Bedzyk et al., *J. Biol. Chem.*, 265:18615 (1990); Chaudhary et al., *Proc. Natl. Acad. Sci.* 87:9491 (1990)). The SAbFvs used in the present invention may be of two types depending on the relative order of the VH and VL domains: VH-1-VL or VL-1-VH (where "1" represents the linker). These SAbFvs lack the constant regions (Fc) present in the heavy and light chains of the native antibody. In another aspect of the present invention, the SAbFv fragment may be fused to all or a portion of the constant domains of the heavy chain, and the resulting extracellular domain is joined to the cytoplasmic domain via an appropriate transmembrane domain that will permit expression in the host cell. The resulting chimeric receptors differ from the SAbFvs, described above, in that upon binding of antigen they initiate signal transduction via their cytoplasmic domain.

To aid in the proper folding and efficient expression of the chimeric receptors, the antibody-derived extracellular domains may be connected at their C-terminal end to one of a number of membrane hinge regions which are a normal part of membrane-bound immunoglobulin molecules. For example, the eighteen amino acids of the IGHG3 M1 exon may be used (Bensmana and Lefranc, *Immunogenet.* 32:321–330 (1990)). The TM domain is attached to the C-terminal end of the membrane hinge. It is also contemplated that membrane hinge sequences may be used to connect non-antibody derived extracellular domains to the transmembrane domains to increase chimeric receptor expression.

Various naturally occurring receptors may also be employed as extracellular domains, where the receptors are associated with surface membrane proteins, including cell differentiation (CD) antigens such as CD4, CD8, cytokine or hormone receptors or adhesion molecules. The receptor may be responsive to a natural ligand, an antibody or fragment thereof, a synthetic molecule, e.g., drug, or any other agent which is capable of inducing a signal. Thus, in addition to CD receptors, ligands for receptors expressed on cancer cells could supply the extracellular domain of the chimeric receptors of the invention. For example human Heregulin (Hrg) a protein similar in structure to Epidermal Growth Factor (EGF), has been identified as a ligand for the receptor $Her_2$ which is expressed on the surface of breast carcinoma cells and ovarian carcinoma calls (Holmes et al., *Science* 256:1205–1210 (1992)). The murine equivalent is the "Neu" protein (Bargman et al., *Nature* 319:226–230 (1986)). The extracellular domain of Hrg could be joined to the CD28 or CD4 transmembrane domain and the CD28 co-stimulatory receptor cytoplasmic domain to form a chimeric construct of the invention to augment the effector function of T cells to kill breast carcinoma cells. In addition, either member of a ligand/receptor pair, where one is expressed on a target cell such as cancer cell, a virally infected cell or an autoimmune disease cause cell may be used as an extracellular domain in the present invention. Moreover, receptor-binding domains of soluble protein ligands or portions thereof could be used as extracellular domains. Binding portions of antibodies, cytokines, hormones or serum proteins can also be used. Alternatively, soluble components of the cytokine receptors such as IL-6R, IL-4R and IL-7R can form the extracellular domains (Boulay and Paul, *Current Biology* 3:573–581 (1993)).

In addition, "hybrid" extracellular domains can be used. For example, two or more antigen-binding domains from antibodies of different specificities, two or more different ligand-binding domains, or a combination of these domains can be connected to each other by oligo- or polypeptide linkers to create multispecific extracellular ligand binding domains. These domains can be used to create co-stimulatory chimeric receptors of the invention which will respond to two or more different extracellular ligands. The extracellular domain may consist of a CD receptor, such as CD4, joined to a portion of an immunoglobulin molecule, for example the heavy chain of Where a receptor is a molecular complex of proteins, where only one chain has the major role of binding to the ligand, it will usually be desirable to use solely the extracellular portion of the ligand binding protein. Where the extracellular portion may complex with other extracellular portions of other proteins or form covalent bonding through disulfide linkages, one may also provide for the formation of such dimeric extracellular region. Also, where the entire extracellular region is not required, truncated portions thereof may be employed, where such truncated portion is functional. In particular, when the extracellular region of CD4 is employed, one may use only those sequences required for binding of gp120, the HIV envelope glycoprotein. In the case in which Ig is used as the extracellular region, one may simply use the antigen binding regions of the antibody molecule and dispense with the constant regions of the molecule (for example, the Fc region consisting of the CH2 and CH3 domains).

In some instances, a few amino acids at the joining region of the natural protein may be deleted, usually not more than 30, more usually not more than 20. Also, one may wish to introduce a small number of amino acids at the borders, usually not more than 30, more usually not more than 20. The deletion or insertion of amino acids will usually be as a result of the needs of the construction, providing for convenient restriction sites, ease of manipulation, improvement in levels of expression, or the like. In addition, one may wish to substitute one or more amino acids with a different amino acid for similar reasons, usually not substituting more than about five amino acids in any one domain. The cytoplasmic domain will generally be from about 50 to 500 amino acids, depending upon the particular domain employed. The transmembrane domain will generally have from about 25 to 50 amino acids, while the extracellular domain will generally have from about 50 to 500 amino acids.

Normally, the signal sequence at the 5' terminus of the open reading frame (ORF) which directs the chimeric protein to the surface membrane will be the signal sequence of the extracellular domain. However, in some instances, one may wish to exchange this sequence for a different signal sequence. However, since the signal sequence will be removed from the protein, being processed while being directed to the surface membrane, the particular signal sequence will normally not be critical to the subject invention. Similarly, associated with the signal sequence will be a naturally occurring cleavage site, which will also normally be the naturally occurring cleavage site associated with the signal sequence or the extracellular domain.

Ligands for binding to the extracellular domain can be antigens including viral proteins, e.g. gp120 and gp41 envelope proteins of HIV, envelope proteins from the Hepatitis B and C viruses, the gB and other envelope glycoproteins of human cytomegalovirus (CMV), the envelope proteins from the Kaposi's sarcoma-associated herpes virus, and surface proteins found on cancer cells, e.g. the IL-14 receptor, CD19 and CD20 for B cell lymphoma, the Lewis Y and CEA antigens for a variety of carcinomas, the Tag72 antigen for breast and colorectal cancer, EGF-R for lung cancer and the HER-2 proteins which is often amplified in human breast and ovarian carcinomas. For other receptors, the receptors and ligands of particular interest are CD4, where the ligand is the HIV gp120 envelope glycoprotein, and other viral receptors, for example ICAM, which is the receptor for the human rhinovirus, and the related receptor molecule for poliovirus.

The chimeric constructs, which encode the chimeric receptor protein according to this invention are prepared in conventional ways. Since, for the most part, natural sequences may be employed, the natural genes may be isolated and manipulated, as appropriate, so as to allow for the proper joining of the various domains. Thus, one may prepare the truncated portion of the sequence by employing the polymerase chain reaction (PCR), using appropriate primers which result in deletion of the undesired portions of the gene. Alternatively, one may use primer repair, where the sequence of interest may be cloned in an appropriate host. In either case, primers may be employed which result in termini, which allow for annealing of the sequences to result in the desired open reading frame encoding the chimeric protein. Thus, the sequences may be selected to provide for restriction sites which are blunt-ended, or have complementary overlaps. During ligation, it is desirable that hybridization and ligation does not recreate either of the original restriction sites.

If desired, the extracellular domain may also include the transcriptional initiation region, which will allow for expression in the target host. Alternatively, one may wish to provide for a different transcriptional initiation region, which may allow for constitutive or inducible expression, depending upon the target host, the purpose for the introduction of the subject chimeric protein into such host, the level of expression desired, the nature of the target host, and the like. Thus, one may provide for expression upon differentiation or maturation of the target host, activation of the target host, or the like.

A wide variety of promoters have been described in the literature, which are constitutive or inducible, where induction may be associated with a specific cell type or a specific level of maturation. Alternatively, a number of viral promoters are known which may also find use. Promoters of interest include the β-actin promoter, SV40 early and late promoters, immunoglobulin promoter, human cytomegalovirus promoter, and the Friend spleen focus-forming virus promoter. The promoters may or may not be associated with enhancers, where the enhancers may be naturally associated with the particular promoter or associated with a different promoter.

The sequence of the open reading frame may be obtained from genomic DNA, cDNA, or be synthesized, or combinations thereof. Depending upon the size of the genomic DNA and the number of introns, one may wish to use cDNA or a combination thereof. In many instances, it is found that introns stabilize the mRNA. Also, one may provide for non-coding regions which stabilize the mRNA.

A termination region will be provided 3' to the cytoplasmic domain, where the termination region may be naturally associated with the cytoplasmic domain or may be derived from a different source. For the most part, the termination regions are not critical and a wide variety of termination regions may be employed without adversely affecting expression.

The various manipulations may be carried out in vitro or may be introduced into vectors for cloning in an appropriate host, e.g., E. coli. Thus, after each manipulation, the resulting construct from joining of the DNA sequences may be cloned, the vector isolated, and the sequence screened to insure that the sequence encodes the desired chimeric protein. The sequence may be screened by restriction analysis, sequencing, or the like. Prior to cloning, the sequence may be amplified using PCR and appropriate primers, so as to provide for an ample supply of the desired open reading frame, while reducing the amount of contaminating DNA fragments which may have substantial homology to the portions of the entire open reading frame.

The chimeric construct may be introduced into the host cell in any convenient manner. Techniques include calcium phosphate or DEAE-dextran mediated DNA transfection, electroporation, protoplast fusion, liposome fusion, biolistics using DNA-coated particles, transfection, and infection, where the chimeric construct is introduced into an appropriate virus, e.g. retrovirus, adenovirus, adeno-associated virus, Herpes virus, Sindbis virus, papilloma virus, particularly a non-replicative form of the virus, or the like. In addition, direct injection of naked DNA or protein- or lipid-complexed DNA may also be used to introduce DNA into cells.

Once the target host cell has been transformed, integration will usually result. However, by appropriate choice of vectors, one may provide for episomal maintenance. A large number of vectors are known which are based on viruses, where the copy number of the virus maintained in the cell is low enough to maintain the viability of the cell. Illustrative vectors include SV40, EBV and BPV.

Once one has established that the transformed host cell expresses the chimeric protein as a surface membrane protein in accordance with the desired regulation and at a desired level, one may then determine whether the transmembrane protein is functional in the host to provide for the desired co-stimulatory signal induction.

The effects of co-stimulation in lymphocytes can be measured by a variety of techniques known to those skilled in the art. For example, augmentation of proliferation can be determined by measuring the incorporation of either tritiated thymidine or orotic acid to measure DNA synthesis following ligand binding to the co-stimulatory chimeric receptor of the invention. The incorporation of bromodeoxyuridine into newly synthesized DNA can be measured by immunological staining and the detection of dyes, or by ELISA (Enzyme-linked immunosorbent assay)(Doyle et al., *Cell and Tissue Culture: Laboratory Procedures*, Wiley, Chichester, England, (1994)). The mitotic index of cells can be determined by staining and microscopy, by the fraction labeled mitoses method or by FACS analysis (Doyle et al., supra, (1994); Dean, *Cell Tissue Kinet.* 13:299–308 (1980); Dean, *Cell Tissue Kinet.* 13:672–681 (1980)). The increase in cell size which accompanies progress through the cell cycle can be measure by centrifugal elutriation (Faha et al., *J. Virol* 67:2456–2465 (1993)). Increases in the number of cells may also be measured by counting the cells, with or without the addition of vital dyes. In addition, signal transduction can also be measured by the detection of phosphotyrosine, the in vitro activity of tyrosine kinases from activated cells, c-myc induction, and calcium mobilization.

TCR binding results in the induction of CD69 expression and cytokine secretion. The ability of a co-stimulatory chimeric receptor of the invention to provide co-stimulation with suboptimal doses of a ligand that stimulates the TCR, is measured by a restoration of CD69 induction and augmented cytokine secretion as described, for example, in the examples, infra.

The subject chimeric receptors may be used to augment the proliferation, and effector function (including cytolysis and cytokine secretion) of immune cells and increase resistance of those cells to anergy. For example, the co-stimulatory chimeric receptors of the invention can be used to deliver cytokines in vitro and in vitro. One measure of T cell activation is the production of cytokines. This is true for both CD4 and CD8 T cells. Moreover, cytokine production is also susceptible to anergy when T cells are stimulated via the TCR without co-stimulation through CD28. Another aspect of CD28 co-stimulation is its ability to augment cytokine production by increasing transcription of cytokine genes and stabilizing cytokine mRNAs. CD4+T cells in addition to CD8+ T cells expressing chimeric receptors may be of particular interest because they have a greater capacity for cytokine production. Any number of cytokines are of interest because of their potential relationships to certain disease states, but in particular the presence of IL-2, IL-4, and $\gamma$-IFN production is important because of their immunomodulatory activities, TNF for its anti-tumor effects, and IFN-$\alpha$ for its anti-viral effects.

The chimeric receptors may be introduced into cells that already contain a chimeric effector function receptor that stimulates effector function upon contact with a target ligand. The two chimeric constructs may respond to the same or different ligands. Alternatively, a hybrid co-stimulatory chimeric receptor may be used which contains both a co-stimulatory signaling domain and an effector function signaling domain. These cells would respond to a single target ligand by proliferating, expressing effector functions such as cytolysis and cytokine production and demonstrating increased resistance to anergy. Thus, these lymphocytes can be activated by any group of cells which contain specific membrane proteins or antigens which may be distinguished from the membrane proteins or antigens on normal cells. For example, neoplastic cells, virus-infected cells, parasite-infected cells, or any other diseased cells would be targets for receptor- containing lymphocytes.

Among the lymphocytes which can be used to treat human disease are cytotoxic CD8+ T cells (CTLs) which have been engineered with chimeric receptors containing extracellular domains which recognize specific antigens and can be used to augment proliferation and/or killing of infected cells in a variety of viral, and parasitic diseases, where the infected cells express the antigens from the pathogen. In particular, co-stimulatory chimeric receptor-CTLs would be particularly effective against viral diseases where transplanted autologous CTLs have shown some efficacy, such as CMV (Reusser et al., *Blood* 78:1373–1380 (1991), Riddell et al., *Science* 257:238–241 (1992)) or where explanted and expanded CTLs continued to have cytolytic activity against virally infected cells, such as HIV (Lieberman et al., *Aids Res. and Human Retroviruses* 11:257–271 (1995)). These chimeric receptors can be constructed with extracellular domains which recognize the viral envelope proteins. For example, SAbs which recognize either gp120 or gp41, or the CD4 extracellular domain which recognizes gp120 can be used to engineer HIV-specific CTLs. Chimeric receptor-CTLs can also be engineered for use against other viruses, such as Hepatitis B virus, Hepatitis C virus, Kaposi's sarcoma associated Herpes virus, the Herpes Simplex viruses, Herpes Zoster virus, and papilloma viruses. Another target for the engineered CTLs are neoplastic cells which express cancer-specific neoantigens or over-express specific membrane proteins. Examples include the IL-14 receptor, CD19 and CD20 for B cell lymphoma, the Lewis Y and CEA antigens for a variety of carcinomas, the Tag72 antigen for breast and colorectal cancer, EGF-R for lung cancer, and the HER-2 protein which is often amplified in human breast and ovarian carcinomas. Chimeric receptor-CTLs can also be used to target autoimmune cells in the treatment of autoimmune diseases such as Systemic Lupus Erythematosis (SLE), myasthenia gravis, diabetes, rheumatoid arthritis, and Grave's disease.

CD4 $^+$ helper T cells (THs) engineered with chimeric receptors containing extracellular domains which recognize specific antigens can also be used to treat human disease. In particular, lymphokine production by chimeric receptor-THs may be effective against cancer cells and mycobacterial infections, including *Mycobacterium avium*, *Mycobacterium tuberculosis* and *Mycobactium leprae*.

Various cell types containing the chimeric constructs described above may be grown in an appropriate nutrient medium for expansion or may be expanded directly in the body via signaling through the chimeric receptors, depending on the cell type, and used in a variety of ways.

Additional types of cells that would benefit from the introduction of the chimeric receptors of the invention include cells that have genes previously introduced or simultaneously introduced with a chimeric receptor which may serve in protein production or to correct a genetic defect. Production of proteins may include growth factors, such as, erythropoietin, G-CSF, M-CSF, and GM-CSF, epidermal growth factor, platelet derived growth factor, human growth factor, transforming growth factor, etc; lymphokines, such as the interleukins.

The recipient of genetically modified allogeneic cells can be immunosuppressed to prevent the rejection of the transplanted cells. In the case of immunocompromised patients, no pretransplant therapy may be required. Another alternative source of cells to be transplanted are so-called "universal donor" cells which have been genetically engineered so that they do not express antigens of the major histocompatibility complex or molecules which function in antigen presentation.

High-titer retroviral producer lines are used to transduce the co-stimulatory chimeric receptor constructs into autologous or allogeneic human T-cells, hematopoietic stem cells or other cells, described above through the process of retroviral mediated gene transfer as described by Lusky et al. in *Blood* 80:396 (1992).

A wide variety of target hosts may be employed, normally cells from vertebrates, more particularly, mammals, desirably domestic animals or primates, particularly humans. The subject chimeric constructs may be used for the investigation of particular pathways controlled by signal transduction, for initiating cellular responses employing different ligands, for example, for inducing activation of a particular subset of lymphocytes, where the lymphocytes may be activated by particular surface markers of cells, such as neoplastic cells, virally infected cells, or other diseased cells, which provide for specific surface membrane proteins which may be distinguished from the surface membrane proteins on normal cells. The cells may be further modified so that expression cassettes may be introduced, where activation of the genetically modified cell will result in secretion of a particular product. In this manner, one may provide for directed delivery of specific agents, such as interferons, TNF's, perforans, naturally occurring cytotoxic agents, or the like, where the level of secretion can be greatly enhanced over the natural occurring secretion. Furthermore, the cells may be specifically directed to the site using injection, catheters, or the like, so as to provide for localization of the response.

The subject invention may find application with effector cells such as lymphocytes including cytotoxic lymphocytes (CTL), Natural killer cells (NK), tumor-infiltrating-lymphocytes (TIL) or other cells which are capable of releasing cytokines or killing target cells when activated. Thus, diseased cells, such as cells infected with HIV, HTLV-I or II, cytomegalovirus, hepatitis B or C virus, mycobacterium avium, etc., or neoplastic cells, where the diseased cells have a surface marker associated with the diseased state may be made specific targets of the effector cells. In particular, diseased cells that lack the appropriate co-stimulatory ligands are targets for the cells expressing the co-stimulatory chimeric receptors of the invention. By providing a receptor extracellular domain, e.g., CD4, which binds to a surface marker of the pathogen or neoplastic condition, e.g., gp120 for HIV, the cells may serve as therapeutic agents. By modifying the cells further to prevent the expression or translocation of functional Class I and/or II MHC antigens, the cells will be able to avoid recognition by the host immune system as foreign and can therefore be therapeutically employed in any individual regardless of genetic background. Alternatively, one may isolate and transfect host cells with the subject constructs and then return the transfected host cells to the host.

Other applications include transduction of host cells from a given individual with retroviral vector constructs directing the synthesis of the chimeric construct. By transduction of such cells and reintroduction into the patient one may achieve autologous gene therapy applications.

In addition, suitable host cells include hematopoietic stem cells, which develop into effector cells with both myeloid and lymphoid phenotype including granulocytes, mast cells, basophils, macrophages, natural killer (NK) cells and T and B lymphocytes. Introduction of the chimeric constructs of the invention into hematopoietic stem cells thus permits the induction of effector functions such as cytotoxicity, cytokine production, proliferation and differentiation of various cell types derived from hematopoietic stem cells providing a continued source of effector cells to fight various diseases. The zeta subunit of the T cell receptor is associated not only with T cells, but is present in other cytotoxic cells derived from hematopoietic stem cells. Therefore, because stem cells transplanted into a subject via a method such as bone marrow transplantation exist for a lifetime, a continued source of effector cells is produced by introduction of the chimeric receptors of the invention into hematopoietic stem cells. Effector cells derived from gene-modified stem cells will express a chimeric effector function and/or a co-stimulatory chimeric receptor, and will be expected to have enhanced capacity to fight virally infected cells, cells expressing tumor antigens, cells responsible for autoimmune disorders, and have increased resistance to anergy. Additionally, introduction of the chimeric receptors into stem cells with subsequent expression by both myeloid and lymphoid cytotoxic cells may have certain advantages in immunocompromised individuals such as patients with AIDS. This is because the maintenance of the lymphoid cytotoxic cells ($CD8^+$) and the continued function of helper T cells ($CD4^+$) may be impaired in AIDS patients due to a failure of natural co-stimulatory mechanisms.

The chimeric receptor constructs of the invention are introduced into hematopoietic stem cells followed by bone marrow transplantation to permit expression of the chimeric receptors in all lineages derived from the hematopoietic system. High-titer retroviral producer lines are used to transduce the chimeric receptor constructs, for example CD4/CD28, into both murine and human T-cells and human hematopoietic stem cells through the process of retroviral mediated gene transfer as described by Lusky et al. in *Blood* 80:396 (1992). For transduction of hematopoietic stem cells, the bone marrow is harvested using standard medical procedures and then processed by enriching for hematopoietic stem cells expressing the CD34 antigen as described by Andrews et al. in *J. Exp. Med.* 169:1721 (1989). These cells are then incubated with the retroviral supernatants in the presence of hematopoietic growth factors such as stem cell factor and IL-6. The bone marrow transplant can be autologous or allogeneic, and depending on the disease to be treated, different types of conditioning regimens are used (see, Surgical Clinics of North America 66:589 (1986)). The recipient of the genetically modified stem cells can be treated with total body irradiation, chemotherapy using cyclophosphamide, or both to prevent the rejection of the transplanted bone marrow. In the case of immunocompromised patients, no pretransplant therapy may be required because there is no malignant cell population to eradicate and the patients cannot reject the infused marrow. In addition to the gene encoding the chimeric receptor, additional genes may be included in the retroviral construct.

The following examples are by way of illustration and not by way of limitation.

EXPERIMENTAL

EXAMPLE 1

Construction of CD4–CD28 Chimeric Receptor

PCR was used to amplify the extracellular and transmembrane portions of human CD28 from a cDNA library of the human T cell line Jurkat (ClonTech) using oligonucleotides 3 and 4 (FIG. 2). A DNA fragment containing the human CD4 gene was obtained by digesting the plasmid pIK1.1CD4 a plasmid described in U.S. Pat. No. 5,359,046 to Capon et al. with EcoRI and NarI. The CD28 fragment was digested with BamHI and NarI, and the two fragments were ligated together and inserted into the pIK1.1 plasmid as described in U.S. Pat. No. 5,359,046, which had been cut with EcoRI and Bgl II by simultaneous double ligation. This yielded a new plasmid, pIK1.1CD4–CD28 which contained the entire coding sequence of human CD4 juxtaposed to the coding sequence of human CD28. The integrity of the new construct was verified by DNA sequencing (Sanger et al., *Proc. Natl. Acad. Sci. USA* 74:5463–5467 (1977)). From this template the CD4/CD28 chimeric receptors were made by oligonucleotide directed mutagenesis (Zoller and Smith, *Nucleic Acids Res.* 10:6487–6500) (1982). Oligonucleotides were designed to create new junctions at the desired sites within the CD4 and CD28 cDNAs (FIG. 2). Using this technique three CD4/CD28 chimeric sequences were created: CH28-1 consists of the extracellular and transmembrane domains of human CD4 fused to the cytoplasmic domain of human CD28 (oligonucleotides 10 and 11); CD28-2 consists of the extracellular domain of CD4 fused to the transmembrane and cytoplasmic domains of CD28 (oligonucleotide 5); and CH28-3 consists of the extracellular domain of CD4 fused to a portion of the extracellular domain plus the entire transmembrane and cytoplasmic domains of CD28 (oligonucleotide 6). These constructs are depicted in FIG. 1A. The portion of the extracellular domain of CD28 contains a cysteine residue (position 141) which is important for the formation of homodimers of CD28 at the cell surface. The pIK1.1plasmid vectors containing the CD4/CD28 fusions (CH28-1, 2, 3) and a selectable marker were created by blunt-end cloning of a HincII fragment of pUCRNeoG (Hudziak et al., *Cell* 31:137–146 (1982)) containing the neomycin phosphotransferase (neo$^r$) gene into pIKCH28-1, pIKCH28-2, and pIKCH28-3 which were cut with SspI. The resulting vectors contain the CD4/CD28 chimeric sequences whose expression is driven by a CMV promoter and the neo$^r$gene driven by the RSV LTR. This vector will confer resistance to the drug G418 when expressed in eukaryotic cells.

Construction of CD8-zeta chimeric receptors

Plasmid vectors encoding CD8-zeta chimeric receptors were created by oligonucleotide-directed mutagenesis using as templates DNA encoding the human CD8α gene (ATCC No. 59565, *Mol. Cell. Biol.* 8:2837–2947 (1988)) and the plasmid CD4-F3 (pIK1.1.CD4-F3) chimeric receptor as described in U.S. Pat. No. 5,359,046. A fragment containing the CD8α cDNA was amplified from the plasmid EBO-pCD.Leu2 using oligonucleotides 12 and 13 (FIG. 2). The PCR product was cut with BstEII and EcoRI to give a 2.3 kb fragment containing the entire coding sequence for CD8α. This fragment was inserted between the BstEII and EcoRI sites of pIK1.1CD4-F3 to generate the plasmid pIK1.1CD8-CD4-F3. Oligonucleotides were designed to create a new junction between CD8α and CD4 sequences at the start of the CD4 transmembrane region and the human CD8α C-terminus of the extracellular region, giving rise to the CD8-F3/A construct (oligonucleotide 14, FIG. 2). In like manner, CD8-F3/B (oligonucleotide 15) was created by joining the CD8α transmembrane domain directly to the zeta cytoplasmic domain. Thus, the CD8-F3/A chimeric receptor contains the CD8α extracellular domain, the transmembrane domain of CD4, and the cytoplasmic domain of CD3 zeta. CD8-F3/B consists of the extracellular and transmembrane domains of CD8α and the cytoplasmic domain of CD3 zeta.

The CD8-F2 chimeric sequence was created in like manner by inserting an EcoRI-BstEII fragment containing CD8-F3 into the vector pIK1.1.CD4-F2 as described in U.S. Pat. No. 5,359,046 and using oligonucleotide-directed mutagenesis (oligonucleotide 16, FIG. 2) to create a chimeric sequence where the extracellular domain of CD8α is fused to the transmembrane and cytoplasmic domains of CD3 zeta. The CD8-F2, CD8-F3/A, and CD8-F3/B sequences were then cloned into the EBV-based expression vector p220.2pIK1.1F3 by replacing a HindIII-SfiI fragment of p220.2pIK1.1.F3 containing the F3 sequences with HindIII-SfiI fragments containing CD8-F2, CD8-F3/A, or CD8-F3/B. The p220.2pIK1.1.F3 plasmid was constructed by first inserting a HindIII-AvrII fragment of pIK1.1between the HindIII and XbaI sites of p220.2 (Yates et al., *Nature* 313:812–815 (1985)) to give p220.2pIK1.1, and then inserting a HindIII-SfiI fragment from pIK1.1.F3 between the HindIII and SfiI sites of p220.2pIK1.1 to give p220.2pIK1.1.F3. The CD8-zeta constructs are depicted in FIG. 1B.

Antibodies

The OKT3, OKT4A, and OKT8 monoclonal antibodies to human CD3, CD4, and CD8α respectively, were obtained from Ortho Diagnostics Systems, Raritan, N.J. Leu3A monoclonal antibodies which recognize human CD4 and the Leu23 antibody to human CD69 were obtained from Becton-Dickinson Immunocytometry Systems, San Jose, Calif. The antibody W6/32 recognizes an invariant determinant expressed on human HLA Class I antigens. The mouse IgG2a myeloma protein (Litton Bionetics, Kensington, Md.) was used as a control antibody for FACS analysis.

Cell lines and Transfections

The human leukemic T cell line Jurkat was maintained in RPMI 1640 supplemented with 10% fetal bovine serum (FBS), glutamine, penicillin, and streptomycin). Jurkat cell lines and clones transfected with the CH28 vectors (CH28-1, -2, -3 and CH2-1, CH2-2 and CH2-3) were passaged in the above medium with the addition of G418 (Geneticin, Gibco, Grand Island, N.Y.) at 2mg/ml. Electroporation of the pIK1.1.CH28-neo and p220pIK1.1.CD8 (CD8-zeta) vectors into Jurkat T cells was performed in a Gene Pulser (Bio-Rad, Richmond, Calif.) using a voltage of 250 V and a capacitance of 960 µF with 20 µg of plasmid DNA per 10$^7$cells. After transfection with pIKCH28-neo vectors, cells were grown for two days in RPMI before transferring to G418-containing medium. Clones of transfected cells were obtained by limiting dilution and screened for CD8 or CH28 (CD4) surface expression by flow cytometry (see below). Jurkat cells transfected with the CD8-zeta vector were passaged in 200 µg/ml hygromycin-containing medium and cloned by limiting dilution.

Flow Cytometry

Approximately 1×10$^6$ cells/condition were stained with saturating concentrations of antibodies directly conjugated to the fluorochrome fluorescein isothiocyanate or with unlabeled antibodies followed by a fluorescein-conjugated goat anti-mouse IgG, and analyzed using a Becton-Dickinson FACScan instrument.

CD4-CD28 chimeric receptors provided co-stimulation for CD3/TCR stimulation in Jurkat T cells The chimeric CD4/CD28 constructs described above were transfected by electroporation into Jurkat cells and the transfected cells were selected in G418 and cloned by limiting dilution. Expression of the CD4/CD28 chimeric receptor on Jurkat cell clones was quantified by flow cytometry using anti-CD4 antibodies. Jurkat T cell clones expressing comparable levels of each of the CD4/CD28 chimeric receptors, CH28-1, CH28-2, and CH28-3, were obtained. The ability of the CH28 chimeric receptors to function as co-stimulatory molecules was evaluated using the induction of the T cell activation antigen CD69 as an indicator (Testi et al., *J. Immunol.* 142:1854–1860). Flow cytometry revealed a very low degree of basal CD69 expression on non-stimulated cells. Maximal levels were induced on all cells with phorbol myristate acetate (PMA), an activator of protein kinase C. Stimulation of the TCR by anti-CD3 antibodies also resulted in the induction of CD69 expression on Jurkat T cells. At concentrations of anti-CD3 below 25 ng/ml no induction of CD69 was observed. Under these conditions addition of anti-CD4 antibodies, which stimulate the CD4/CD28 chimeric receptor, restored the induction of CD69 expression. Stimulation of the CD4/CD28 receptor alone did not induce CD69 expression, nor did the control antibody, W6/32. These data show that all three of the CD4/CD28 chimeric receptors (CH28-1, CH28-2, CH28-3) function as co-stimulatory molecules together with CD3/TCR stimulation in Jurkat T cells.

Function of the CD4CD28 chimeric receptor in Jurkat cells expressing a zeta chimeric receptor To test whether the CD4/CD28 chimeric receptor could provide co-stimulation for zeta chimeric receptor stimulation, Jurkat T cells expressing the CH28-1 chimeric receptor (Jurkat CH28-1 clone #2) were transfected with the CD8-zeta chimeric receptors described above. Transfected Jurkat CH28-1 cells were selected in hygromycin, cloned by limiting dilution, and analyzed for CD8-zeta expression by flow cytometry using anti-CD8 antibodies (OKT8). Jurkat CH28-1 cells expressing each of the three CD8-zeta receptors were obtained. One clone expressing CD8-F2 (F10) and one expressing CD8-F3/B (B6) were evaluated for co-stimulation by the chimeric CD4/CD28 receptor. The ability of the CH28-1 receptor to provide co-stimulation with suboptimal doses of anti-CD3 (TCR stimulation) and anti-CD8 antibodies (CD8-zeta stimulation) were compared. Anti-CD4 treatment restored CD69 induction in CH28-1/CD8-zeta expressing Jurkat cells stimulated with a suboptimal dose of anti-CD3. Moreover, anti-CD4 antibodies also restored CD69 induction in cells stimulated with low doses of anti-CD8. These results demonstrate that CD4/CD28 chimeric receptors can provide co-stimulation for zeta-based chimeric receptors as well as for CD3/TCR stimulation. Thus, chimeric receptors employing the cytoplasmic domain of CD28 can be used in combination with chimeric effector signal function receptors, e.g. CD4/zeta, to generate cells with two functional signaling receptors providing both of the signals necessary for optimal T cell activation.

EXAMPLE 2

Function of CD4/CD28 chimeric receptor in primary human CD+ T cell lines

CD4/CD28 chimeric receptors were introduced into primary human CD8+ T cells using retrovirus vectors. To accomplish this, the CH28-3 chimeric sequence was cloned into the retrovirus vector pRTD2.2svg.F3 (e$^{31}$) (Finer et al. (1994) Blood 83:43) to create the retroviral vector pRTD2.2svg.CH28-3 (e$^{31}$). This vector has the retroviral genomic RNA expression driven by a CMV promoter, and CH28-3 expression driven by the MMLV LTR. pRTD2.2svg.CH28-3 DNA. Primary human CD8+ T cells in active growth are transduced with the CH28-3 gene by the Kat retroviral transduction packaging system (Finer et al., *Blood*, supra).

Transduced T cells were analyzed for expression of the CD4/CD28 chimeric receptor (CH28-3) by flow cytometry using anti-CD4 antibodies (Leu3A). The ability of CH28-3 to provide co-stimulation in primary human CD8+ T cells was tested in an in vitro assay. Activation of T cells by stimulation of the TCR with anti-CD3 requires the presence of APCs (ref.), for example normal peripheral blood mononuclear cells (PBMC) which have been rendered incapable of cell division by irradiation or treatment with DNA synthesis inhibitors such as mitomycin C. To test for co-stimulation by the CD4/CD28 chimeric receptor, anti-CD4 antibodies were used in place of PBMC in experiments measuring proliferation ($^3$H-TdR incorporation), CD69 induction (FACS), and cytokine production (ELISA). T cells are treated with unlabeled anti-CD3 antibodies alone or anti-CD3 antibodies plus anti-CD4 antibodies (to bind the CH28-3 receptor) for 30 min. at 4° C. The cells are washed extensively to remove unbound antibodies and incubated in 24-well tissue culture plates in wells coated with goat anti-mouse IgG at 37° C. Crosslinking of cell surface receptors in this way is sufficient to induce signal transduction. First, induction of CD69 expression will be determined by flow cytometry. T cells treated as described above will be collected after 18 h incubation an analyzed for CD69 expression by staining with a fluorochrome-labeled antibody to CD69. It is expected that at suboptimal doses of anti-CD3, little to no induction of CD69 expression will be observed. Under these conditions the additional treatment of cells with anti-CD4 antibodies, binding to the CH28-3 receptor should restore the induction of CD69 expression. Stimulation with PMA serves as a positive control. Another important feature of T cell activation is the production of cytokines, for example IL-2, IL-4, GM-CSF, and γ-IFN. The ability of CH-28-3 expressing T cells to secrete cytokines in response to anti-CD3 stimulation with or without CH28-3-mediated co-stimulation is determined using the experimental system described above. Second, cytokine production is determined by harvesting the culture supernatant from the cells after 48 h and measuring cytokine levels by ELISA (Quantikine kits, R & D Systems, Minneapolis, Minn.). As a control for these experiments T cells are cultured with soluble anti-CD3 and APCs. Thus, in these experiments, co-stimulation by binding of the CH28-3 chimeric receptor should result in increased levels of cytokine production. The effect of co-stimulation may vary for different cytokines. Third, the ability of CH28-3 bearing T cells to proliferate is determined by measuring incorporation of $^3$H-thymidine between 54–72 h after stimulation. The T cells are stimulated as described above with anti-CD3 antibodies with or without anti-CD4 co-stimulation in 96-well tissue culture plates, with each test re-produced in triplicate. after 54 h in culture, 3H-thymidine is added, and the cells are harvested after 18 h. DNA from the cells is harvested onto glass fiber filters and incorporation of tritium measured by scintillation counting as a measure of DNA synthesis. Co-stimulation by CH28-3 is expected to support T cell proliferation at suboptimal doses of anti-CD3, where little to no response is expected with anti-CD3 alone. Similar experiments are carried out using T cells expressing a zeta-based chimeric receptor in addition to CH28-3. For example, using T cells expressing F15 (SAb-zeta) the same experiments are performed, but where anti-human IgG Fc antibodies are substituted for anti-CD3 to provide primary stimulation via SAb-zeta.

EXAMPLE 3

Increased growth and transduction efficiency of T cells co-stimulated via CH28-3

It has been reported that co-stimulation by anti-CD28 antibodies enhances the growth rate and cloning efficiency of human CD8+ T cells grown in vitro (Riddell and Greenberg, supra, and may augment their capacity for autocrine IL-2 production. Since the use of T cells expressing chimeric receptors for in vivo therapy may require the generation of large numbers (>$10^9$) transduced T cells in vitro prior to infusion, developing a means of increasing the efficiency of this process would be of obvious benefit. First, if cells could be expanded in vitro more rapidly, the initial number of donor cells could be reduced, and the time required to generate the necessary number of cells may be shortened. Second, since retrovirus transduction requires that cells be in an active growth phase for successful integration of provirus, a means of driving a greater proportion of cells into the growth phase of the cell cycle at any given time might increase the efficiency of retroviral transduction. The ability of CD28-based chimeric receptors to perform these functions is tested by introducing the CH28-3 chimeric receptor into human primary CD8+ T cells, and comparing the growth rates of these T cells when stimulated weekly with anti-CD3 and APCs or anti-CD3 plus anti-CD4 plus APCs in the presence of IL-2. The growth rate is determined by determining the number of viable cells present in the cultures and plotting cell number vs. time. The ability to augment retrovirus transduction efficiency is tested by exposing T cells with and without CH28-3 to retrovirus containing the gene for a zeta-based chimeric receptor (e.g., F15) and determining by FACS analysis the percentage of cells expressing the zeta receptor. The expectation is that T cells with CH28-3, when co-stimulated with anti-CD4 antibodies will achieve higher numbers of cells in a shorter period of time than cells stimulated with anti-CD3 alone, and that CH28-3 T cells co-stimulated with anti-CD4 will be transduced with a higher efficiency that those cells stimulated with anti-CD3 alone.

EXAMPLE 4

Construction of a CD4/CD2 Chimeric Receptor

CD4/CD2 chimeric receptors were constructed as described above in Example 1. Oligonucleotides used to amplify CD2 DNA from the cDNA library were oligonucleotides 1 and 2 (FIG. 2). CH2-1 consisted of the extracellular and transmembrane domains of human CD4 fused to the cytoplasmic domain of human CD2; CD2-2 consisted of the extracellular domain of CD4 fused to the transmembrane and cytoplasmic domains of CD2; and CH2-3 consisted of the extracellular domain of CD4 fused to a portion of the extracellular domain plus the entire transmembrane and cytoplasmic domains of CD2. The portion of the extracellular domain of CD2 contains a cysteine residue (position 203) which is important for the formation of homodimers of CD2 at the cell surface. Oligonucleotides used to generate the fusions were as described in FIG. 2. CH2-1: oligonucleotide 7; CH2-2: oligonucleotide 8; CH2-3: oligonucleotide 9. These constructs are depicted in FIG. 1A.

The ability of the three CD4-CD2 chimeric receptors to synergize with the native TCR in the manner of the native CD2 receptor was evaluated by measuring IL-2 secretion. Three representative clones stably expressing the chimeric constructs CH2-1, CH2-2 and CH2-3, respectively, were subject to stimulation via the native CD3/TCR with Mab OKT3 (Ortho) in the presence or absence of native CD2 stimulation with the anti-CD Mab OKT11 (Ortho). At least a 3-fold augmentation of IL-2 production was observed with CD2 co-stimulation as compared to stimulation via the TCR alone. Antibodies directed against the extracellular domain of either of the chimeric CD2 constructs (OKT4) could elicit the same response as that obtained upon stimulation of the native CD2. Specifically, OKT4 in combination with the TCR antibody OKT3 led to augmentation of the TCR signal by at least 3-fold. A similar co-stimulatory response was obtained upon stimulation of all three CD2 chimeric proteins, and was similar to that obtained from the native CD2 receptor. These results indicate that the cytoplasmic domain of CD2 is sufficient for the synergistic effect of CD2 on TCR-mediated T cell activation.

EXAMPLE 5

Protection from anergy by antibody-driven co-stimulation

Stimulation of T cells through the TCR, for example by anti-CD3 antibodies, in the absence of a co-stimulatory signal, such as one delivered via the cytoplasmic domain of CD28, results in a state of specific non-responsiveness called anergy. Anergic T cells may proliferate initially in response to the anergizing signal, but are rendered non-responsive to a second signal given through the TCR (Johnson and Jenkins, supra). Co-stimulation of the TCR and the CD28 receptor protect cells from entering a state of anergy. The ability of the CD28-based chimeric receptors such as CD4/CD28 to protect T cells from becoming anergic is tested as follows: T cells expressing CH28-3 will be stimulated in vitro with antibodies to CD3 bound to a solid surface (tissue culture wells) in the absence of APCs. In parallel these cells are stimulated in wells coated with both anti-CD3 and anti-CD4 (which stimulate the CD4/CD28 receptor). As a control the T cells are stimulated with anti-CD3 in the presence of APCs as described above. After 7–10 days, the cells are stimulated a second time with anti-CD3 and APCs in each case. T cells originally cultured with anti-CD3 alone should fail to proliferate (i.e., incorporate $^3$H-TdR) in response to anti-CD3 ' even under optimal conditions. If the stimulation of the CD28 chimeric receptor affords protection from anergy, T cells expressing CH28-3 stimulated with anti-CD3 and anti-CD4 should respond normally to anti-CD3 in the presence of APCs, in the same manner as cells stimulated originally with anti-CD3 in the presence of APCs.

EXAMPLE 6

Function of CH28-3 in Primary human T cells expressing a zeta-based chimeric receptor Since it has been demonstrated that the CD28 chimeric receptors function in conjunction with zeta-based chimeric receptors (above), this experimental model can also be used with primary T cells expressing both a zeta-based chimeric receptor and CH28-3. Primary human CD8+T cells expressing a SAb-zeta chimeric receptor (F15, as described in U.S. Pat. No. 5,359,046) are transduced with the CH28-3 chimeric receptor by retrovirus-mediated gene transfer as described above. Cells expressing both chimeric receptors are identified by FACS analysis using anti-human IgG Fc antibodies to detect the SAb-zeta (F15) receptor, and anti-CD4 antibodies to detect CH28-3. These cells are tested for their susceptibility to anergy via CD3/TCR stimulation and F15 stimulation as described above using anti-CD3 antibodies, or anti-Fc antibodies (Caltag Laboratories, So. San Francisco, Calif.) to stimulate the SAb-zeta receptor, in the absence of APCs, together with anti-CD4 antibodies for co-stimulation.

EXAMPLE 7

Protection from anergy induced by Co-stimulation-Deficient Tumor Cells

Both F15 and CH28-3 recognize antigens displayed by 293 cells transfected with the HIV envelope gene. These cells stimulate proliferation and serve as targets for lysis by cytotoxic T cells expressing F15 (Roberts et al., *Blood*, 84(9):2878–2889 (1994)). APCs or target cells which are fixed (e.g., by paraformaldehyde) are not able to provide co-stimulation even though they express the appropriate antigen for recognition by T cells (Johnson and Jenkins, supra and Otten and Germain *Science* 251:1228–1231 (1991)). The ability of CH28-3 to protect T cells from anergy by exposure to fixed target cells is tested by comparing the responses of T3/F15 T cells with and without CH28-3 to live 293env cells after prior exposure to fixed 293 env cells. CD8+ F15 T cells are co-cultured with an experimentally determined number of live, mitomycin-treated or paraformaldehyde fixed 293 cells expressing the HIV envelope protein, in the presence of IL-2. After 7–10 days the cells are challenged by re-exposure to live 293 env cells. First, the ability of CD8/F15 cells to proliferate in response to live, mitomycin-treated 293 env cells is determined by thymidine incorporation assay. Second, cytokine production in response to 293 env is measured under the same experimental conditions by ELISA as described above. Third, the antigen-specific cytolytic function of the cells is determined using the JAM assay for target cell lysis (Matzinger, *J. Immunol. Methods* 145:185 (1991)). Briefly, 293 env cells are labeled overnight with 3H-thymidine, and plated in 96-well plates the next day, together with CD8/F15 cells. Lysis of the 293 env cells is determined by counting the amount of radioactive DNA released into the supernatant by the damaged cells in 6 h. The expectation is that CD8/F15 cells without CH28-3 will become anergic when exposed to fixed 293 env cells, due to lack of co-stimulation, and will fail to proliferate, produce cytokines, or kill 293 env targets upon re-exposure. In contrast, CD8/F15 cells which express CH28-3 will receive the necessary co-stimulation from fixed 293env, and will proliferate, produce cytokines, and kill normally when re-exposed to live 293 env.

EXAMPLE 8

Protection from anergy induced by cell-free virus particles

A potential use of T cells expressing chimeric receptors which recognize HIV antigens is to introduce them into HIV-infected individuals as a form of anti-viral therapy. In vivo the T cells will encounter large amounts of soluble antigen in the patient's serum which may be capable of rendering these anergic to stimulation by their true targets, HIV-infected cells. For example, there is sufficient soluble gp120 shed by virus particles and infected cells in the serum of HIV seropositive individuals to prime CD4+ positive T cells to undergo apoptosis, a programmed cell death mechanism, when they are stimulated by antigen or polyclonal mitogens (Banda et al., *J. Exp. Med.* 176:1099–1106 (1992)). The susceptibility of T cells armed with anti-HIV chimeric receptors to anergy induced by soluble gp120 or cell-free virus particles is tested by incubating CD8/F15 cells, with or without CH28-3, with soluble gp120 (e.g. 50 ng/ml) or with heat-inactivated culture supernatant from HIV-infected T cells which contains various amounts of HIV by p24 content, e.g. 500 pg/ml of p24 gag (Roberts et al., (1994) supra). Treatment of the cells with soluble antigens is in the absence of APCs. After 7–10 days, the cells will be exposed to 293 env cells, and their biological responses (i.e., proliferation, cytokine production, and cytotoxicity) are measured by standard assays as described above. CD8/F15 cells co-expressing CH28-3 are protected from anergy induced by soluble antigens, but those without the CD28-based chimeric receptor are susceptible.

EXAMPLE 9

Enhancement of Anti-tumor immunity in vivo in transgenic mice expressing CH28-3

The murine T cell lymphoma line EL-4 produces nodular tumors when introduced into syngeneic mice (Chen et al., *J. Exp. Med.* supra). EL-4 cells lack expression of the B7 ligand for CD28 and do not elicit protective immunity except by repeated injection of large numbers of irradiated tumor cells (ibid.). In contrast, EL-4 cells transduced to express B7 are unable to form tumors in syngeneic mice. Instead, injection of mice with EL-4/B7 cells causes the regression of existing EL-4 tumors and confers lasting protective immunity against subsequent injections with B7[31] EL-4 cells (ibid.). The ability of CD28-based chimeric receptors to augment the immune response to a relatively non-immunogenic tumor is tested in vivo using mice which are transgenic for the expression of CH28-3. CH28-3 DNA is introduced into the genome of C57BL/6 mice, which are syngeneic to EL-4 cells, by micro-injection of the transgenic expression vector pIK.Mcd2(en/dcr)CH28-3. In this vector the CH28-3 chimeric co-receptor is expressed under the control of the murine mammary leukemia virus (MMLV) promoter and a transcriptional control region of the CD2 gene, designated the enhancer-dcr region (Lake et al., *EMBO* 9:3129–3136 (1990)). The CD2 en/dcr transcriptional control region drives expression of the CD2 gene in lymphocytes, and has been shown to confer high level tissue-specific position-independent expression of the gene when introduced into the germ line of mice (Lang et al. *Nucleic Acids Res.* 19:5851–5856 (1991)). Therefore, integration of the pIK.Mcd2 (en/dcr)CH28-3 vector into the genome of C57BL/6 mice results in expression of the CH28-3 chimeric co-receptor in murine lymphocytes. Mice whose lymphocytes express high levels of the CH28-3 receptor were identified by analyzing blood and lymphoid tissue by FACS with antibodies to human CD4. Such mice will be injected with non-manipulated EL-4 cells or EL-4 cells expressing the HIV envelope protein. The ability of these cells to form tumors in CH28-3 transgenic and normal mice is compared. The expectation is that stimulation of the CH28-3 receptor on transgenic T cells by HIV env expressed on the EL-4 cells will stimulate an immune response to EL-4 cells which will be absent in normal mice. Thus, the CH28-3 transgenic animals should reject the EL-4 cells and show no or greatly reduced formation of tumors. The non-manipulated EL-4 cells should form tumors in both kinds of mice. These experiments demonstrate the ability of CD28-based chimeric receptors to provide co-stimulation in a situation in which antigen-responsive cells are present, but the natural immune response is insufficient due to a lack of co-stimulation.

EXAMPLE 10

Increase functional activity of adoptively transferred cells in vivo

For these experiments a small animal model is used to study the function of primary human T cells expressing zeta-based and CD28-based chimeric receptors in vivo. Two human disease models are established in SCID mice (Bosman and Carroll, *Annu. Rev. Immunol*, 9:323–350 (1991)): (i) a tumor model using human tumor cells, and (ii) a virus infection model using HIV-infected human PBL (McCune et al., ibid 399–430; Mosier et al., *Nature* 335:256–259 (1988)). For example, the human B lymphoblastoid cell line Raji produces lethal tumors when engrafted into SCID mice (Malkovska et al., *Cancer Res.* 52:5610–5616 (1992)). Raji cells expressing HIV envelope also produce tumors in SCID mice. Raji env cells provide a convenient model for testing human T cells bearing chimeric receptors which recognize HIV envelope determinants such as CD4-zeta, Sab-zeta (F15), and CD4-CD28 (CH28-3). T cells expressing a zeta-based UR with or without CH28-3 are introduced into SCID mice together with antigen-bearing tumor cells. The longevity of cells introduced with tumor cells are compared to the survival of cells in mice with out tumor cells, by isolating the human T cells from the blood and lymphoid tissue of SCID mice at sequential time intervals. The number of human T cells present is determined, as well as expression of the chimeric receptors, and the ability to proliferate and to kill appropriate target cells in vitro. One expectation would be that in the presence of tumor cells which fail to provide normal co-stimulation the lifespan and biological activity of the chimeric receptor T cells will be prolonged if those cells possess a CD28-based chimeric receptor in addition to a zeta-based receptor both of which recognize the same target cells. The mice can also be analyzed for tumor progression, metastases, and the like. Similarly, SCID mice engrafted with HIV-infected human PBL are used to assess the functional activity of chimeric receptor bearing T cells in an in vivo model of HIV infection. T cells expressing zeta-based chimeric receptors with and without a CD28-based chimeric receptor are introduced into SCID mice harboring HIV-infected human PBL. The longevity of the cells and biological activity against HIV is measured as described above, along with viral load in the mice, by p24 assay (Coulter Immunology, Hialeah, Fla.) and persistence of CD4 T cells.

What is claimed is:

1. A method for augmenting an immune cell effector function by providing a co-stimulatory signal to a host cell comprising:
   a) introducing a DNA expressing a chimeric co-stimulatory receptor protein into a host cell under conditions suitable for expression of said chimeric receptor protein to produce receptor-expressing cells; and
   b) contacting said receptor-expressing cells with a target ligand, wherein said chimeric receptor protein comprises in the N-terminal to c-terminal direction:
   an extracellular ligand-binding domain that binds said target ligand;
   a transmembrane domain; and
   a cytoplasmic co-stimulatory domain; wherein said cytoplasmic domain is CD2 or CD28; and wherein said extracellular domain is not obtained from CD2 or CD28.

2. The method of claim 1 wherein the extracellular domain is CD4.

3. The method of claim 1 wherein the host cell is an immune cell.

4. The method of claim 1 wherein the host cell is a lymphocyte or hematopoietic stem cell.

5. The method of claim 1 wherein the effector function is cytolytic activity of the host cell.

6. The method of claim 1 wherein the effector function is cytokine production.

7. The method of claim 1 wherein the effector function is resistance of the host cell to anergy.

8. The method of claim 1 wherein the effector function is proliferation of the host cell.

9. The method of claim 1 wherein the effector function is differentiation, maturation or both of the host cell.

10. The method of claim 1 wherein the host cell expresses a chimeric effector function signaling receptor protein comprising an extracellular ligand binding domain, a transmembrane domain and a cytoplasmic effector function signaling domain.

11. The method of claim 1, wherein said protein further comprises a cytoplasmic effector signaling domain.

* * * * *

UNITED STATES PATENT AND TRADEMARK OFFICE
CERTIFICATE OF CORRECTION

PATENT NO. : 5,686,281
DATED : November 11, 1997
INVENTOR(S) : Margo R. Roberts

It is certified that error appears in the above-indentified patent and that said Letters Patent is hereby corrected as shown below:

Col. 3, line 63, delete "257;217" and insert --257:217--.

Col. 10, line 43, after "of", insert --Ig.--.

Col. 13, line 39, delete the 2nd occurrence of "vitro", and insert therefor --vivo--.

Col. 14, line 48, delete "Mycobactium" and insert --Mycobacterium--.

Col. 19, line 57, delete "$e^{31}$" and insert therefor --$e^-$--; and line 59, delete "$e^{31}$" and insert therefor --$e^-$--.

Col. 20, line 22, delete "an", and insert therefor --and--.

Col. 31, line 38, delete "c-" and insert therefor --C- --.

Signed and Sealed this

Fourteenth Day of July, 1998

Attest:

BRUCE LEHMAN

Attesting Officer

Commissioner of Patents and Trademarks